(12) United States Patent
Meister

(10) Patent No.: US 8,868,195 B2
(45) Date of Patent: Oct. 21, 2014

(54) PHASE TRIGGERED ENVELOPE SAMPLER

(75) Inventor: Dirk Meister, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1108 days.

(21) Appl. No.: 12/701,015

(22) Filed: Feb. 5, 2010

(65) Prior Publication Data

US 2010/0204755 A1 Aug. 12, 2010

Related U.S. Application Data

(60) Provisional application No. 61/150,482, filed on Feb. 6, 2009.

(51) Int. Cl.
*A61N 1/36* (2006.01)

(52) U.S. Cl.
CPC .................................. *A61N 1/36032* (2013.01)
USPC .................................. 607/56; 607/55; 607/57

(58) Field of Classification Search
CPC .................. A61N 1/0541; A61N 1/36032
USPC ........................................... 607/55–57
See application file for complete search history.

(56) References Cited

U.S. PATENT DOCUMENTS

| | | | |
|---|---|---|---|
| 4,284,856 A | 8/1981 | Hochmair et al. | 179/107 E |
| 4,428,377 A | 1/1984 | Zollner et al. | 128/419 |
| 4,515,158 A | 5/1985 | Patrick et al. | 128/419 R |
| 5,215,085 A | 6/1993 | Von Wallenberg-Pachaly | 128/420.6 |
| 5,601,617 A | 2/1997 | Loeb et al. | 607/56 |
| 5,938,691 A | 8/1999 | Schulman et al. | 607/57 |
| 6,175,767 B1 | 1/2001 | Doyle, Sr. | 607/57 |
| 6,219,580 B1 | 4/2001 | Faltys et al. | 607/57 |
| 6,289,247 B1 | 9/2001 | Faltys et al. | 607/57 |
| 6,295,472 B1 | 9/2001 | Rubinstein et al. | 607/55 |

(Continued)

FOREIGN PATENT DOCUMENTS

| | | | |
|---|---|---|---|
| WO | WO 99/35882 | 7/1999 | H04R 25/00 |
| WO | WO 99/49815 | 10/1999 | A61F 2/18 |

(Continued)

OTHER PUBLICATIONS

Grayden, et al, "A Cochlear Implant Speech Processing Strategy Based on an Auditory Model", *Proceedings of the 2004 Intelligent Sensors* Sensors Networks and Information Processing Conference, Dec. 14-17, 2004; pp. 491-496.

(Continued)

*Primary Examiner* — Carl H Layno
*Assistant Examiner* — Eugene Wu
(74) *Attorney, Agent, or Firm* — Sunstein Kann Murphy & Timbers LLP

(57) ABSTRACT

A method of generating electrode stimulation signals for an implanted electrode array is described. An acoustic audio signal is processed to generate band pass signals which each represent an associated band of audio frequencies. For each band pass signal, fine time structure information is extracted to determine a sequence of phase event signals. For each sequence of phase event signals, when the number of phase event signals reaches a channel pitch rate factor, a signal limiting period without signals is introduced to produce a modified sequence of phase event signals. Each modified sequence of phase event signals is weighted with a channel amplitude value in order to generate a set of electrode stimulation signals for the implanted electrode array.

13 Claims, 3 Drawing Sheets

(56) References Cited

U.S. PATENT DOCUMENTS

| | | | |
|---|---|---|---|
| 6,594,525 B1 | 7/2003 | Zierhofer | 607/57 |
| 6,600,955 B1 | 7/2003 | Zierhofer | 607/57 |
| 7,072,717 B1* | 7/2006 | Wolf et al. | 607/57 |
| 7,209,789 B2 | 4/2007 | Zierhofer | 607/57 |
| 2005/0107843 A1 | 5/2005 | McDermott et al. | 607/57 |
| 2005/0192646 A1 | 9/2005 | Grayden et al. | 607/57 |
| 2005/0203589 A1 | 9/2005 | Zierhofer | 607/57 |
| 2005/0222644 A1* | 10/2005 | Killian et al. | 607/57 |
| 2006/0052841 A1 | 3/2006 | Daly et al. | 607/57 |
| 2006/0080087 A1* | 4/2006 | Vandali et al. | 704/207 |
| 2006/0217784 A1 | 9/2006 | Kitazawa et al. | 607/57 |
| 2006/0227986 A1 | 10/2006 | Swanson et al. | 381/312 |
| 2006/0265061 A1 | 11/2006 | Kwon et al. | 623/10 |
| 2007/0156202 A1 | 7/2007 | Zierhofer | 607/57 |
| 2007/0239227 A1* | 10/2007 | Fridman | 607/57 |
| 2009/0254150 A1* | 10/2009 | Zierhofer | 607/57 |
| 2009/0312820 A1* | 12/2009 | Nie et al. | 607/57 |

FOREIGN PATENT DOCUMENTS

| | | | | |
|---|---|---|---|---|
| WO | WO 01/19135 | 3/2001 | | H04R 25/00 |
| WO | WO 01/19304 | 3/2001 | | A61F 11/04 |
| WO | WO 2006/119069 | 11/2006 | | |

OTHER PUBLICATIONS

Kral, A., et al, "Spatial resolution of cochlear implants: the electrical field and excitation of auditory afferents", *Hearing Research*, vol. 121 (1998, pp. 11-28.

Loizou, P.C., "Signal Processing for Cochlear Prosthesis: A Tutorial Review", *IEEE*, Jan. 1997, pp. 881-885; 0-7803-3694-1/97.

Loizou, P.C., "Signal-Processing Techniques for Cochlear Implants", *IEEE Engineering in Medicine and Biology*, May/Jun. 1999, pp. 34-46.

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

Secker-Walker, H., et al, "Time-domain analysis of auditory-nerve-fiber firing rates", *J. Acoust. Soc. Am.* 88(3), pp. 1427-1436 (1990).

Sit., J., et al, "A Low-Power Asynchronous Interleaved Sampling Algorithm for Cochlear Implants that Endoes Enelope and Phase Information", *IEEE Trans Biomed Eng.*, Jan. 2007; 54(1), pp. 138-149.

Vandali, A., et al, "Pitch ranking ability of cochlear implant recipients: A comparison of sound-processing strategies", *Accoust Soc. Am.*, May 2005; 117(5); pp. 3126-3138.

Wilson, B.S., et al, "Comparative Studies of Speech Processing Strategies for Cochlear Implants", *Laryngoscope*, vol. 96, No. 10, pp. 1068-1077, Oct. 1988.

Wilson, B. S., et al, "Better speech recognition with cochlear implants", *Nature*, vol. 352, pp. 236-238, Jul. 18, 1991.

Wilson, B. S., et al, "Seventh Quarterly Progress Report; Speech Processors for Auditory Prostheses", *Center for Auditory Prosthesis Research*, pp. 1-69, 1994.

Wilson, B. S., et al, "Temporal Representations With Cochlear Implants", *The American Journal of Otology*, 18:530-534, 1997.

Ziese, M., et al, "Speech Understanding with the CIS and the n-of-m Strategy in the MED-EL COMBI 40+ System", *ORL*, 2000;62:321-329.

European Patent Office, Simona Koleva, International Search Report and Written Opinion, PCT/US2010/023302, dated Apr. 16, 2010.

* cited by examiner

PHASE TRIGGERED ENVELOPE SAMPLER

This application claims priority from U.S. Provisional Patent Application 61/150,482, filed Feb. 6, 2009; incorporated herein by reference.

FIELD OF THE INVENTION

The present invention relates to medical implants, and more specifically to signal processing in cochlear implant systems.

BACKGROUND ART

Cochlear implant users report good system performance in quiet background conditions, but that performance degrades significantly with the addition of background noise. Similarly, most cochlear implant users have difficulty listening to music. As pitch is an important element of music, the perception of temporal fine structure in the audio signal is important for enjoying music.

The cochlear implant stimulation rate is recognized by cochlear implant users as pitch percept up to some given limit. For example, Baumann and Nobbe, *Pulse Rate Discrimination With Deeply Inserted Electrode Arrays*, Hearing Research 2004; 196 (1-2):49-57; incorporated herein by reference, describes that the ability to discriminate rate changes was limited to base rates up to about 283 pps. They also found no difference for basal and apical regions of the cochlea.

One cochlear implant stimulation strategy that transmits fine time structure information is the FSP strategy by MED-EL. Zero crossings of the band pass filtered time signals are tracked, and at each negative to positive zero crossing, a Channel Specific Sampling Sequence (CSSS) is started. Typically CSSS sequences are only applied on the first one or two most apical channels, covering the frequency range up to 200 or 330 Hz.

Another stimulation coding strategy that shows good performance in noisy conditions is known as Continuous Interleaved Sampler (CIS). For example, Kiefer J et al., *Speech Understanding In Quiet And In Noise With The CIS Speech Coding Strategy (MED-EL Combi-40) Compared To The Multipeak And Spectral Peak Strategies (Nucleus)*, ORL J Otorhinolaryngol Relat Spec., 1996 May-June; 58(3):127-35; incorporated herein by reference described: "In the inter-subject comparisons, the mean results in noise with the CIS strategy were superior to both the MPEAK and the SPEAK strategies." But the CIS strategy is based solely on the envelope of the audio signal and phase information is disregarded so that fine time structure is not transmitted.

U.S. Pat. No. 7,039,466, incorporated herein by reference, describes a method for reducing the stimulation rate on basal channels: "[A]pically-located regions within the cochlea are stimulated at a reduced rate in order to conserve power." This stimulation strategy attempts to reduce power consumption and does not make use of phase information from the audio signal. In addition, the order of rate-reduction is based on the refractory states of neurons and not on the pitch rate limit of a CI user.

United States Patent Application US 2007/0239227, incorporated herein by reference, describes a similar method for reducing stimulation rate, referred to as Frequency Modulated Stimulation (FMS). The FMS strategy does transmits information at integer multiples of zero-crossings or equivalent frequency counting, but does not restrict the stimulation rate according to a psychophysically measured pitch rate limit.

SUMMARY OF THE INVENTION

Embodiments of the present invention are directed to generating electrode stimulation signals for an implanted electrode array. An acoustic audio signal is processed to generate band pass signals which each represent an associated band of audio frequencies. For each band pass signal, fine time structure information is extracted to determine a sequence of phase event signals. For each sequence of phase event signals, when the number of phase event signals reaches a channel pitch rate factor, a signal limiting period without signals is introduced to produce a modified sequence of phase event signals. Each modified sequence of phase event signals is weighted with a channel amplitude value in order to generate a set of electrode stimulation signals for the implanted electrode array.

In further specific embodiments, the channel amplitude value may be based on sampling the band pass signal envelope. A desired pulse shape, such as a biphasic pulse, may be used for weighting each modified sequence of phase event signals. The signal limiting period may have a predefined duration, or it may have a dynamically determined duration, for example, a phase dependent function may be used for determining the signal limiting period. In some specific embodiments, extracting fine time structure information may be based on zero crossings of the band pass signals.

An embodiment may further more specifically define for each band of frequencies a channel frequency limit and a channel pitch rate limit beyond which pitch perception saturates, wherein the channel pitch rate factor is selected such that the ratio of the frequency limit to the channel pitch rate factor is less than or equal to the pitch rate limit. In some specific embodiments, a phase event counter may be used for determining when the number of phase event signals reaches the channel pitch rate factor.

Embodiments of the present invention also include a computer program product implemented in a computer readable storage medium for generating electrode stimulation signals for an implanted electrode array according to any of the above. Embodiments also include a cochlear implant system operating according to any of the above.

DETAILED DESCRIPTION OF SPECIFIC EMBODIMENTS

Various embodiments of the present invention are directed to a coding strategy for cochlear implants that combines noise-robust envelope sampling with fine time structure speech processing while keeping the rate of the fine structure below the pitch rate perceptual limit. Continuous Interleaved Sampling (CIS) is used to band pass filter an audio signal into multiple channels. The envelope of the band pass signal is determined within each channel (e.g., by Hilbert transformation or rectified low pass filtering), and the envelope within each channel is sampled with a given rate. Interleaved, non-simultaneous stimulation pulses are derived from the sampled envelopes. To ensure that no charge remains on the neuron membranes, charge-balanced biphasic or tri-phasic pulses can be used. The fine time structure processing is extended to higher frequencies while keeping the fine structure rate below the pitch rate perception limit.

A phase-dependent signal limiting period is used to provide an additional temporal fine-structure cue that is presented to the cochlear implant user. Thus, the benefits of a CIS stimulation strategy can be combined with the transmission of fine time structure. The CIS strategy is robust as to noise, and fine time structure provides accurate pitch discrimination and for improved enjoyment of music. The fine time structure is presented through by introducing signal limiting periods into the stimulation signal sequence. These signal limiting periods are correlated to the phase of the band pass signal, e.g. to zero-crossings of the band pass-signal.

An additional frequency cue could be presented when correlating the extent of the signal limiting period with the instantaneous frequency, for example, by covering the time between a zero crossing and half the time span to the succeeding zero crossing (=peak). Since pitch rate saturates for cochlear implant users at values around 300 pps, the fine time structure events can be limited to a rate that corresponds to this limit, ensuring that the time code can be processed by the cochlear users. With this concept, time structure processing can be useful for higher frequency channels compared to the FSP strategy.

Figure 1:
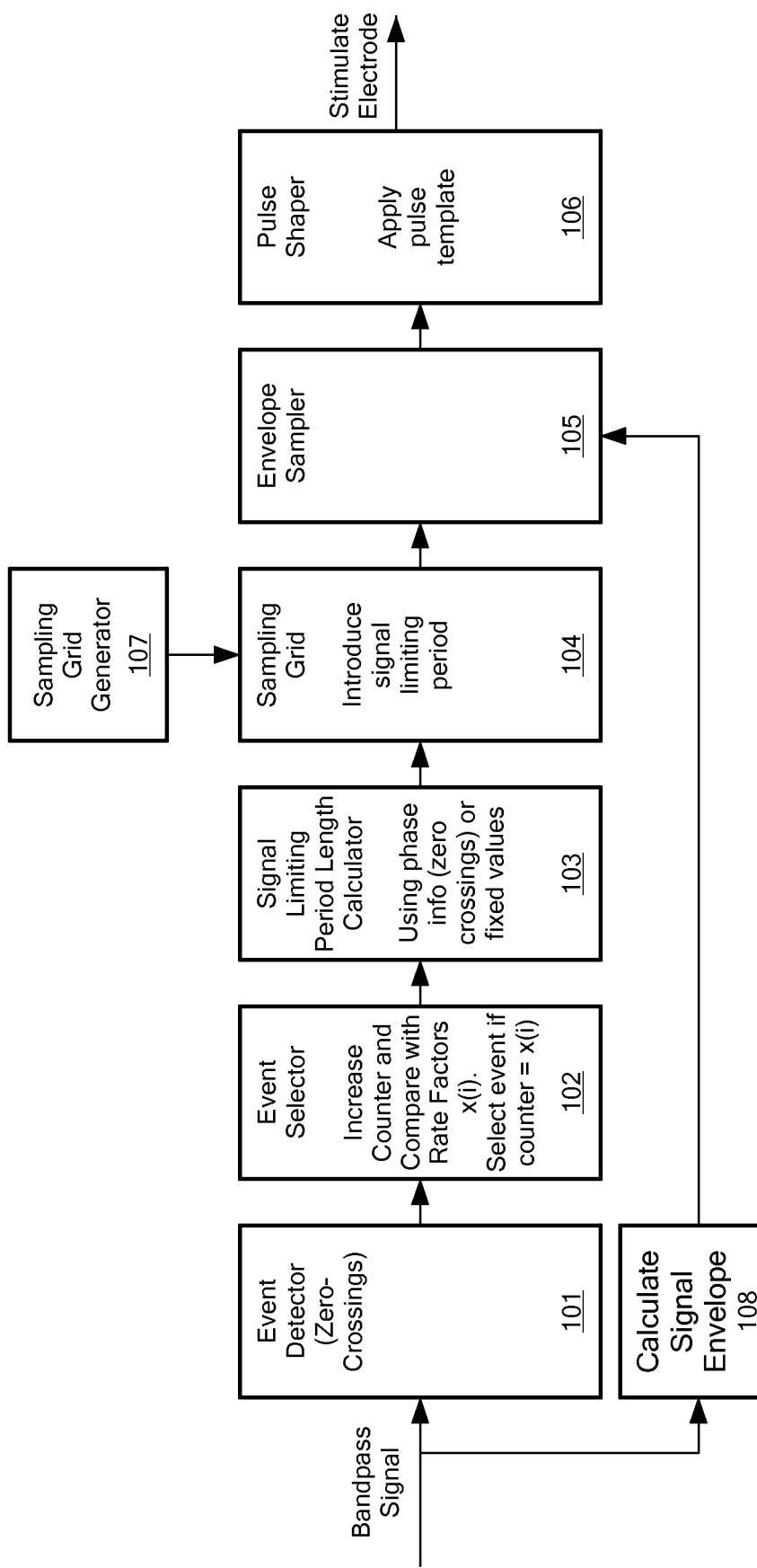
FIG. 1 shows various functional blocks in processing the stimulation signal according to typical embodiments of the present invention.
Figure 2:
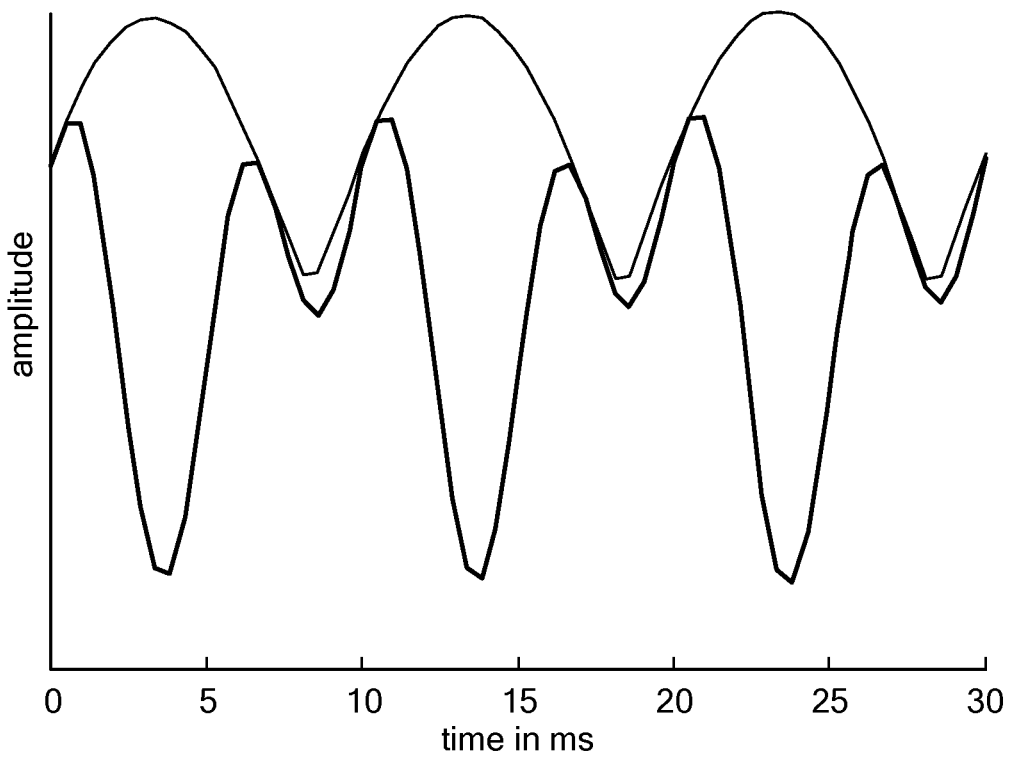
FIG. 2 shows an example of a band pass filtered time signal and envelope of a speech signal.
Figure 3:
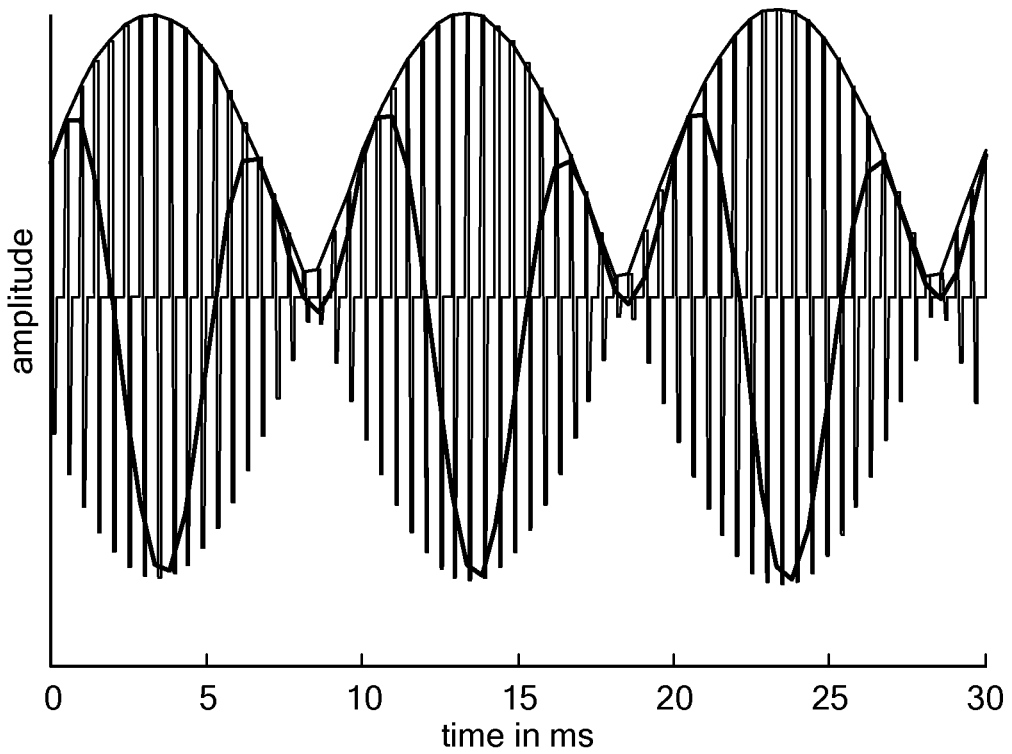
FIG. 3 shows an example of a band pass envelope sampled with biphasic pulses.

FIG. 1 shows various functional blocks in processing the stimulation signal according to typical embodiments of the present invention to generate electrode stimulation signals for an implanted electrode array. An acoustic audio signal is pre-processed by a filter bank to generate band pass signals which each represent an associated band of audio frequencies. For each band pass signal, an event detector 101 extracts fine time structure information to determine a sequence of corresponding phase event signals. For example, the event detector 101 may use a zero crossing detector to detect when the band pass signal transitions from a negative value to a positive value. FIG. 2 shows an example of a band pass filtered time signal and envelope of a speech signal, in this specific case, the syllables "aba" where the band pass filter cut-off frequencies were 100 Hz and 200 Hz. FIG. 3 shows an example of a similar band pass envelope sampled with biphasic pulses as in a CIS stimulation strategy.

To extract fine time structure from the band pass time signal within each channel, an integer value rate-factor x(i) is defined for each channel i, so that:

$$F_{lim}(i)/x(i) \leq R_{lim}(i)$$

where $F_{lim}(i)$ could be, for example, the upper frequency or the center frequency of channel(i), and $R_{lim}(i)$ is the pre-defined pitch-rate limit. This can be restated as:

$$x(i) = \text{floor}(F_{lim}(i)/R_{lim}(i)) \qquad \text{Eq. (1)}$$

The pitch rate factors may be adjusted once during a fitting session and stay constant in the running process. The pitch rate limit can be a predefined fixed value or determined with psychoacoustic experiments individually for each channel and each patient. To determine these patient- and channel-specific pitch rate limits, frequency scaling or discrimination experiments may be performed to determine the limits where pitch saturates with increasing rate.

The next stage in FIG. 1, event selector 102 decides which phase event (e.g., zero crossing) triggers a pitch rate factor modification of the processing. Specifically, for each sequence of phase event signals, when the number of phase event signals reaches a given channel pitch rate factor, event selector 102 introduces a signal limiting period without signals to produce a modified sequence of phase event signals. This may be implemented in the event selector 102 by using a counter whose value is compared to the channel pitch rate factor, and when the counter equals the pitch rate factor, the phase event sequence is selected for modification. For example, if Channel 6 with $F_{lim}(6)=1200$ Hz and $R_{lim}(i)=300$ Hz., then x(6)=4. So every 4th fine-time structure event will be selected.

When a modification is selected, signal limiting period length calculator 103 computes the length of the signal limiting period, and the signal limiting period is introduced into the signal sampling grid 104 created by sampling grid generator 107. The signal limiting period length calculator 103 may set the signal limiting period to have a predefined duration, for example determined with psychoacoustic measurements or calculated with the center frequency of the filter. Or the signal limiting period length calculator 103 may set the signal limiting period to have a dynamically determined duration, for example, a phase dependent function may be used for determining the signal limiting period.

Figure 4:
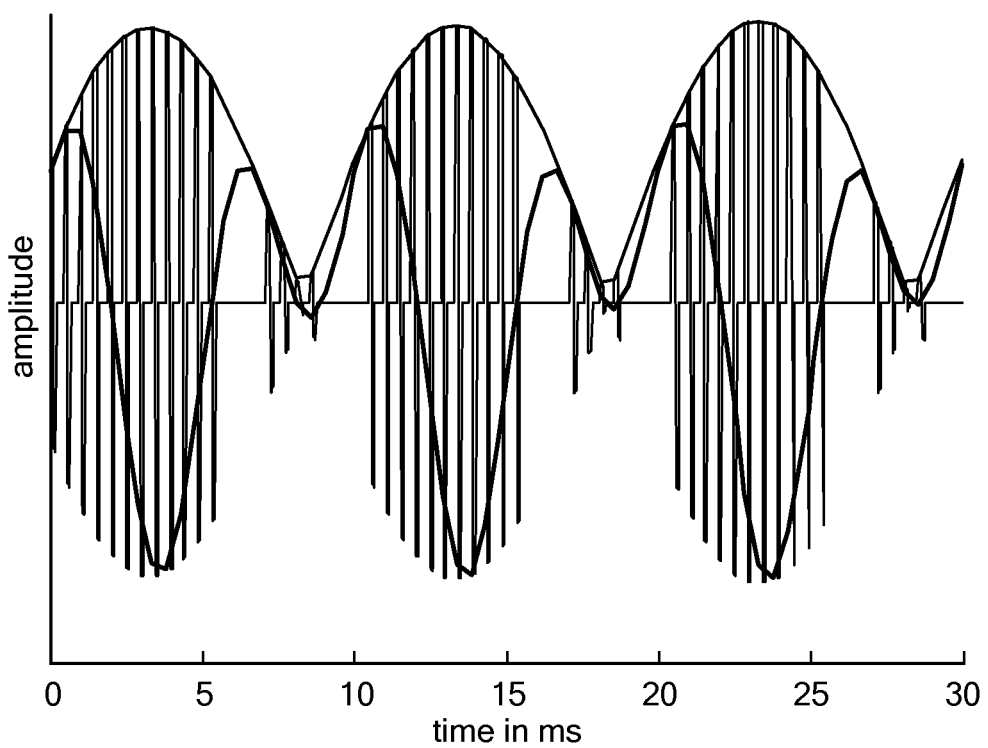
FIG. 4 shows a modified pulse sequence with signal limiting periods according to an embodiment of the present invention.
Figure 5:
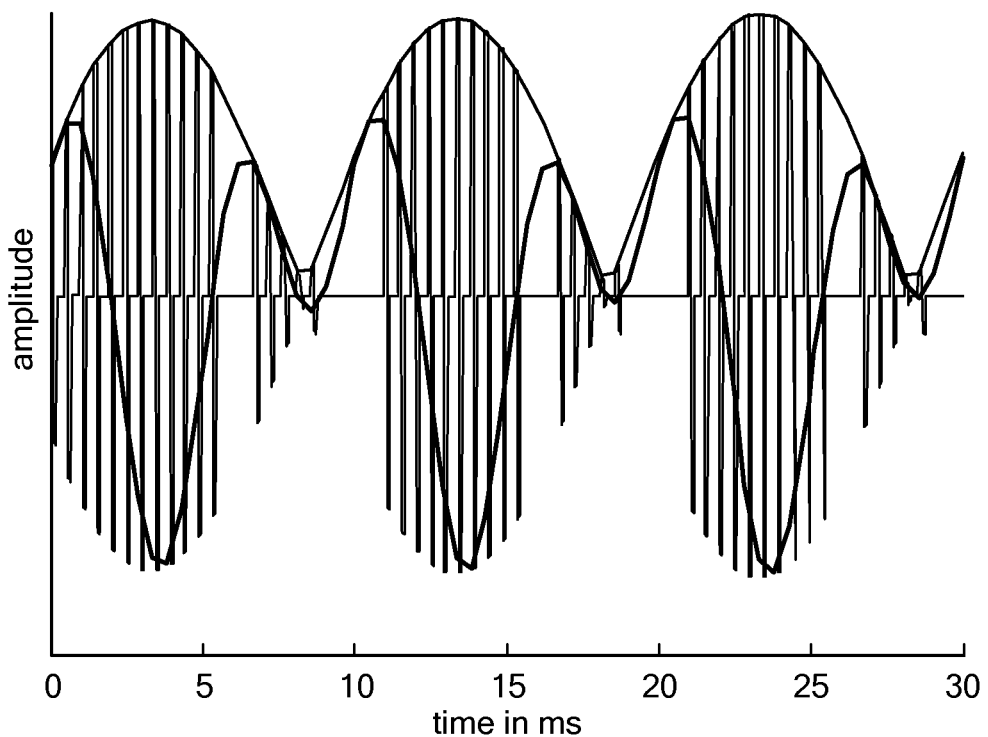
FIG. 5 shows another example where signal limiting periods are calculated from the succeeding zero crossing

FIG. 4 shows a modified pulse sequence with signal limiting periods introduced starting at negative to positive zero-crossings and extending to a fixed length, for example, to a quarter of the band pass center frequency. In another embodiment, the signal limiting period length calculator 103 may set the extent of the signal limiting period as a function of the phase of the time signal, e.g. of the distance of the succeeding (or preceding) zero-crossing or peak within that channel. Thus, the extent of the signal limiting period could reach from the zero-crossing, selected by the rate-factor, up to the next peak of the signal. This means that the first stimulation pulse after a signal limiting period could coincide with a peak of the band pass time signal. This is illustrated in FIG. 5 where the signal limiting periods are calculated as a quarter of the distance of the preceding zero crossing of the band pass signal. Since the last signal limiting period has no succeeding zero-crossing, for that signal limiting period the default value of the quarter of the band pass-center frequency may be used.

Based on the modified sampling grid, each modified sequence of phase event signals is weighted with a channel amplitude value in order to generate a set of electrode stimulation signals for the implanted electrode array. For example, as shown in FIG. 1, envelope sampler 105 samples the band pass signal envelope 108 to determine the channel amplitude value. Pulse shaper 106 then calculates the stimulation signal pulses by weighting of the sampled envelope with the desired pulse shape, e.g., biphasic CIS pulses. Some embodiments could implement these principles with n-of-m type strategies or selected channel groups to achieve higher time grids at the selected channels.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for an implanted electrode array, the method comprising:
   processing an acoustic audio signal to generate a plurality of band pass signals, each of which represents an associated band of audio frequencies;
   for each band pass signal:
   i. extracting fine time structure information to determine a sequence of phase event signals for the band pass signal,
   ii. creating a signal limiting period after a plurality of phase event signals occurs that reaches a channel pitch rate limit characterizing saturation of pitch perception, and
   iii. sampling a band pass envelope at a given sampling rate, except during signal limiting periods, to determine channel amplitude values; and
   generating a set of electrode stimulation signals for the implanted electrode array at the sampling rates for the respective band pass signals, said set of electrode stimulation signals being stimulation pulses weighted with the respective channel amplitude values, wherein for each band pass channel, the generation of electrode stimulation signals is interrupted during each signal limiting period.

2. A method according to claim 1, wherein the signal limiting period has a dynamically determined duration.

3. A method according to claim 2, wherein a phase dependent function is used for determining the signal limiting period.

4. A method according to claim 1, wherein the signal limiting period has a predefined duration.

5. A method according to claim 1, wherein extracting fine time structure information is based on zero crossings of the band pass signals.

6. A method according to claim 1, wherein the set of electrode stimulation signals comprises a sequence of biphasic pulses.

7. A cochlear implant system adapted to use the method according to any of claims 1, 6 and 4-5.

8. A computer program product implemented in a non-transitory, tangible computer readable storage medium for generating electrode stimulation signals for an implanted electrode array, the product comprising:
   program code for processing an acoustic audio signal to generate a plurality of band pass signals, each of which represents an associated band of audio frequencies;
   program code for, for each band pass signal:
   i. extracting fine time structure information to determine a sequence of phase event signals for the band pass signal,
   ii. creating a signal limiting period after a plurality of phase event signals occurs that reaches a channel pitch rate limit characterizing saturation of pitch perception, and
   iii. sampling a band pass envelope at a given sampling rate, except during signal limiting periods, to determine channel amplitude values; and
   program code for generating a set of electrode stimulation signals for the implanted electrode array at the sampling rates for the respective band pass signals, said set of electrode stimulation signals being stimulation pulses weighted with the respective channel amplitude values, wherein for each band pass channel, the generation of the electrode stimulation signals is interrupted during each signal limiting period.

9. A product according to claim 8, wherein the signal limiting period has a dynamically determined duration.

10. A product according to claim 9, wherein a phase dependent function is used for determining the signal limiting period.

11. A product according to claim 8, wherein the signal limiting period has a predefined duration.

12. A product according to claim 8, wherein extracting fine time structure information is based on zero crossings of the band pass signals.

13. A product according to claim 8, wherein the set of electrode stimulation signals comprises a sequence of biphasic pulses.

* * * * *